United States Patent [19]
Takeuchi et al.

[11] Patent Number: 5,947,726
[45] Date of Patent: Sep. 7, 1999

[54] DENTAL PROBE AND DENTAL DIAGNOSIS DEVICE

[76] Inventors: Hideyuki Takeuchi, 9-41 Kyomachi, Fushimi-Ku, Kyoto-shi, Kyoto-fu 612-8083, Japan; Shigeru Kirino, 1330 Ikadachiminamisho-cho, Otsu-shi, Shiga-ken 520-0354, Japan

[21] Appl. No.: 09/088,884

[22] Filed: Jun. 2, 1998

[30] Foreign Application Priority Data

Jun. 2, 1997 [JP] Japan .................................. 9-144304

[51] Int. Cl.$^6$ ...................................................... A61C 19/04
[52] U.S. Cl. .................. 433/72; 128/776; 33/514
[58] Field of Search .................... 433/72, 75, 32, 433/29; 128/776, 777; 33/513, 574

[56] References Cited

U.S. PATENT DOCUMENTS 4,925,268  5/1990  Iyer et al. ............................. 350/96.29
5,000,901  3/1991  Iyer et al. ................................ 264/299
5,516,285  5/1996  Yatcher et al. ............................ 433/72
5,755,571  5/1998  Cowparion .................................. 433/72

*Primary Examiner*—Nicholas D. Lucchesi
*Attorney, Agent, or Firm*—Chadbourne & Parke LLP

[57] ABSTRACT

A dental probe that directly measures pH level and temperature of gum pockets and other diseased parts of the oral cavity is provided. The dental probe has a handle and a needle with a pH sensor and a temperature sensor in the needle tip. The handle permits the dentist to manipulate the needle tip to examine a diseased spot in the mouth, where both pH levels and temperature can be analyzed. The rear part of the handle has a light receptor which remains outside the oral cavity when the needle tip is inserted in the diseased part, creating a path for light through the needle part. The dental probe is attached to a dental diagnosis device that enables processing and readout of pH levels and temperature.

10 Claims, 3 Drawing Sheets

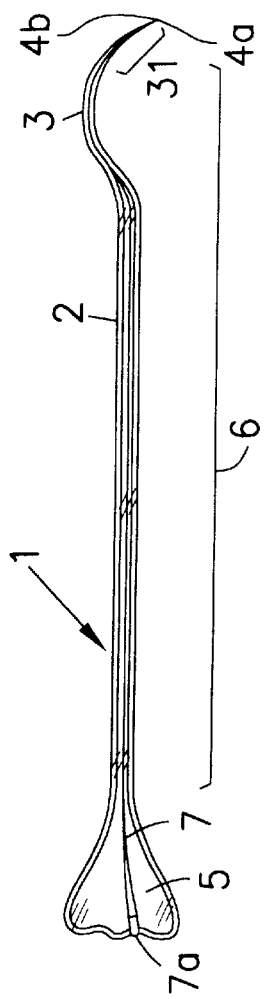
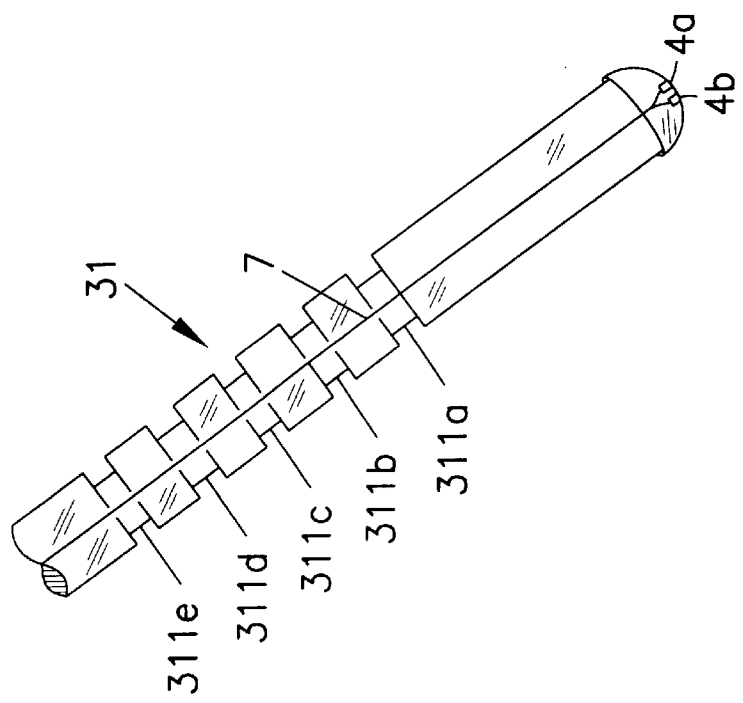
FIG. 1
FIG. 2

DENTAL PROBE AND DENTAL DIAGNOSIS DEVICE

FIELD OF THE INVENTION

This invention relates to a dental probe and diagnosis device for examination of gum pockets and diseased parts of the mouth that can rapidly determine pH levels and temperature at an examined site.

BACKGROUND OF THE INVENTION

Effective treatment and prevention of caries and periodontal disease depends upon the ability to accurately examine and ascertain the condition of a patient's gum pockets. This is especially important in public health or general clinical situations. Caries activity tests for infants, for example, are administered by measuring pH levels of saliva or tartar obtained from gum pockets using the calorimetric method or hydrogen ion concentration. These tests determine the bacterial breeding ratios and the maturation of the diseased part of the gum.

A drawback of both the calorimetric and the hydrogen-ion concentration tests is that they require a relatively large sample quantity. Moreover, it is difficult to take samples of saliva and tartar from infants, and when the sample is not tested immediately after collection, the rapidly changing culture condition makes accurate pH measurement difficult. With existing collection techniques, sample collection to the diseased part of the mouth, such as a gum pocket. It would therefore be desirable to have a device that could directly measure the pH level at the affected part of the gum.

It would also be desirable if the device could measure the temperature of a diseased part of a gum to assist in effective diagnosis and treatment. During a dental operation, it often becomes necessary to monitor the temperature of the spot that is being operated upon, so that the heat generated by friction from the drilling and puncture of teeth and bones does not destroy the surrounding cells. Existing devices do not offer appropriate means to measure temperature, leading dentists to cool the diseased parts based on their own experience. Since this lacks accuracy, a suitable temperature measurement device has been sought.

The design of existing dental probes can be adapted to provide these features. One such existing probe is described in allowed U.S. patent application Ser. No. 08/869,523 to Hideyuki Takeuchi, one of the inventors of the present invention. That probe is designed to measure the depth of the diseased part of a gum pocket. It comprises a handle with a needle on the distal end, wherein the needle has etched gradations on its tip to enable measurement. The needle tip can also probe diseased spots in the oral cavity. The rear part of the probe's handle has a light receptor which remains outside the mouth when the needle tip is inserted in the gum pocket, creating a path for light to the needle and the vicinity of the gum pocket.

That probe can be easily adapted to measure pH levels and temperature. Since the dentist can accurately guide the probe's needle tip to a diseased part of the gum, he can obtain a direct and accurate measurement of the pH level with an electric device at the needle tip. The dentist can also accurately measure temperature with a temperature sensor on the needle tip.

SUMMARY OF THE INVENTION

It is therefore an object of the present invention to provide a dental probe that directly measures pH levels and the temperature of a gum pocket and other diseased parts of the mouth.

In accordance with this and other objects, the dental probe of the present invention has a handle and a needle with a pH sensor. The handle enables the dentist to manipulate the needle tip to examine a diseased spot in the oral cavity. The rear part of the handle has a light receptor which remains outside the oral cavity when the needle tip is inserted in the diseased part, creating a path for light to the needle.

The pH sensor can be N-channel ISFET. The needle tip is also preferably equipped with a temperature sensor. Most of the device except the testing part and the outgoing wiring can have a dielectric coating, and the outgoing wiring can be transparent. The probe preferably has etched gradations on the needle tip in order to permit measurement of the depth of diseased parts, and the needle tip may be hemispherical.

This dental probe, which can directly measure pH levels of diseased oral cavity parts, does not require the collection of saliva. It can be used for infants, ensuring accurate pH measurement without time lag. If required, the probe can measure temperature and depth of a diseased part such as a gum pocket. The probe can take accurate temperature measurements, and cool the precise spot in the oral cavity. The probe can measure depth of the diseased part and monitor progress of the disease, enabling the user to implement an effective treatment plan.

A dental diagnosis device is attached to the aforementioned dental probe. It contains devices to run current to the sensor, record output signals from the sensor, and to display the obtained data. The pH calibration curve can be drawn using buffer solution. The dental diagnosis device can also determine bacterial breeding ratios and maturation. Specific usage of its device includes measurement of hydrogen-ion concentration in saliva and tartar, examination of the contents of gum pockets, and measurement of hydrogen-ion concentration of bacterial containment in the pockets.

BRIEF DESCRIPTION OF THE DRAWINGS

FIG. 1 is a side view of an embodiment of the dental probe.

FIG. 2 is a side view of an embodiment of the needle part of the dental probe.

DETAILED DESCRIPTION OF THE INVENTION

Figure 3:
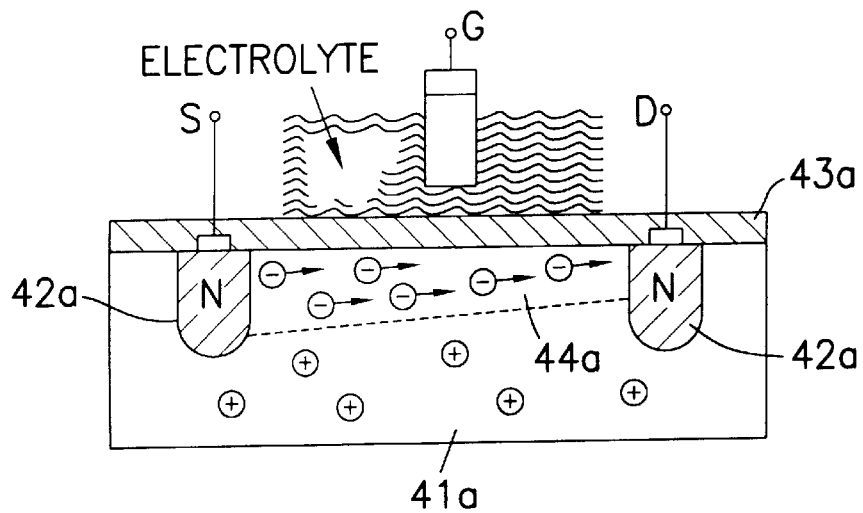
FIG. 3 is an enlarged cross section of an N-channel ISFET structure.

FIG. 1 shows the preferred embodiment of the present invention. The dental probe 1 has a handle 2 with a needle that extends forward and forms a curve 3. The needle tip 31 has a pH sensor 4a and a temperature sensor 4b. By manipulating the handle 2, the dentist guides the tip of the needle 31 to the diseased spot in the oral cavity. The device has a light receptor 5 which remains outside the oral cavity when the needle tip is inserted in a diseased spot, creating a path 6 for light through the needle 31. It is recommended that the outgoing wiring to draw out electric output signal of the pH sensor 4a and the temperature sensor 4b be made with a printed wiring device covering the surface of the light path 6 so that the wires y do not interfere with the light which travels through the path 6. The outgoing wiring 7 is covered with 50–75 μm-thick photosensitive dry film or photo resist film, which prevents the current from running into the oral cavity from the outgoing wiring 7. The outgoing wiring 7, if made of such transparent material as ITO, can run through the light path 6. The output 7a of the outgoing wire 7 is positioned at the end of the light receptor 5.

While FIG. 1 shows the handle 2 in a stick form; the handle is not so limited in shape, so long as it can be held by a hand. The curved extension 3 gives the needle 31 a slight angle against the handle 2 so that the tip does not harm the oral cavity wall or the diseased part when the needle 31 is inserted deeply. However, the device does not necessarily require this curve. The front of the extension 3 with sufficient length, gradually narrows and forms a needle. This is to provide flexibility to avoid harming the oral cavity wall or diseased parts. The light receptor 5 has a large area shaped like a fan in order to maximize reception of light. The light receptor 5 does not have to be in a fan shape as long as it can receive sufficient light. In this figure, the light receptor 5 is positioned behind the handle 2. It can be positioned on the handle 2 as long as it remains outside the oral cavity to take in light when the tip of the needle 31 is inserted into the diseased area. In FIG. 1, the handle 2, the extension 3 and the light receptor 5 are made of transparent material. If the light receptor 5 is located at the handle 2, a transparent material can be used only for the part covering the light receptor 5 and the front of the handle 2. The light path 6 has a characteristic of optic fiber made of core and clad, guiding the light received by the light receptor 5 to the needle 31. The needle 31 then illuminates its surroundings, making the examined area easy to see.

FIG. 2 is a partially enlarged view of the needle 31. The pH sensor 4a and the temperature sensor 4b are at the tip of the needle 31. The surface of the needle 31 has etched gradations (311a to. 311e), marked from its tip towards the handle 2. In this example, the markings are ring-shaped gutters surrounding the needle 31. So long as they are visible, any other markings such as lines will suffice. The gradations do not need to be continuous. In FIG. 2, the markings are 0.5 mm, 3 mm, 2 mm, 3 mm in accordance with the WHO standard to diagnose the progress of the diseased part by reading an appropriate mark to measure the depth.

The transparent material for the light receptor 5 and the light path 6 may be organic material such as polycarbonate or inorganic material such as quartz, although it is not limited to those materials. Fluorescent and dyestuffs can be added to the transparent material so that the gradations (311a–311e) on the needle 31 can be seen better.

The pH sensor 4a can be any kind as long as the element can signal electric output responding to the pH level of the environment at the tip of the needle 31. In this example, N-channel ISFET is used. ISFET has a small chip which can accommodate a narrower needle so that the needle it can be easily inserted into narrow space such as a gum pocket. The high sensitivity of ISFET helps the user obtain accurate information promptly.

As shown in FIG. 3, there are two islands 42a made of N-pattern region. The islands 42a are positioned with some distance near a P-pattern semiconductor substrate 41a, one being Source S and the other Drain D. The surface of substrate 41a has insulating coating 43a. Gate G is positioned opposite the substrate 41a surface.

The principal of pH testing by N-channel ISFET is as follows: In the P-pattern semiconductor substrate 41a here are a large number of positive holes that are plus barriers and a small number of electrons that are minus carriers. The voltage of Gate G is maintained positive. The plus carrier below Gate G in the P-pattern semiconductor substrate moves away from Gate G, forming an N-pattern channel region 44a between the Source island 42a and the Drain island 42a.

The current runs through the N-channel region 44a when voltage is given to Source-Drain. Even when the voltage on Gate G is consistent, presence of electrolyte solution such as saliva near Gate G, hydrogen-ion in the solution will be added to the positive voltage of Gate G. Therefore, the actual voltage on the substrate surface 41a changes in accordance with concentration level of hydrogen-ion in the electrolyte solution.

When the concentration level of hydrogen-ion in the electrolyte solution increases, actual positive voltage becomes higher. That creates a larger N-channel region 44a because the plus carrier moves farther away from the substrate 41a surface. On the other hand, if the hydrogen-ion concentration decreases, actual voltage becomes lower and creates a smaller N-channel region 4a, bringing positive holes as a plus carrier closer to the surface 41a. When voltage between Source and Drain is kept constant, the current which runs through the N-channel region 44a changes according to the change of hydrogen-ion concentration level in the electrolyte solution.

Figure 4:
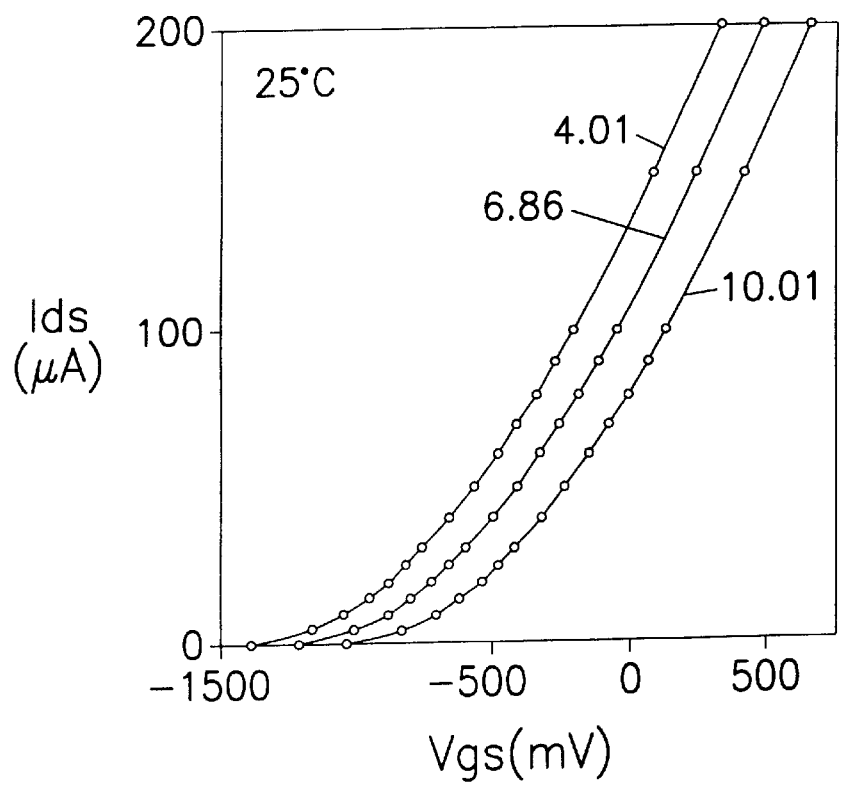
FIG. 4 is a graph showing pH characteristics of the N-channel ISFET.

FIG. 4 is a graph plotting relationship between voltage between Gate G and Source S (Vgs) and voltage between Drain D and Source S (Ids). They are measured at each pH level of 4.01, 6.86, 10.01, buffer solution in which the needle tip 31 of the dental probe 1 has been soaked. In an acid condition where the hydrogen-ion concentration is higher, the Drain current becomes larger. In an alkaline condition where the hydrogen-ion concentration is lower, the Drain current becomes smaller. The graph shows the pH level corresponding to the current (Ids) and the voltage (Vgs) in the region where the current between Drain D and Source S (Ids) is 50 μA and above, and where the voltage between Gate G and Source S (Igs) is 500 mV and above. Given consistent voltage, the pH level accurately corresponds to the size of current, and given consistent current, the pH level accurately corresponds to the size of voltage. From this graph, the calibration curve can be drawn. With the use of N-channel ISFET, pH testing can be administered in such a way.

For a more specific measurement, the pH level is obtained in correspondence to change of voltage (Vgs), with current (Ids) maintained within the rage of 50–100 μA. In this case, pH sensitivity is approximately 50–55 mV/pH.

Figure 5:
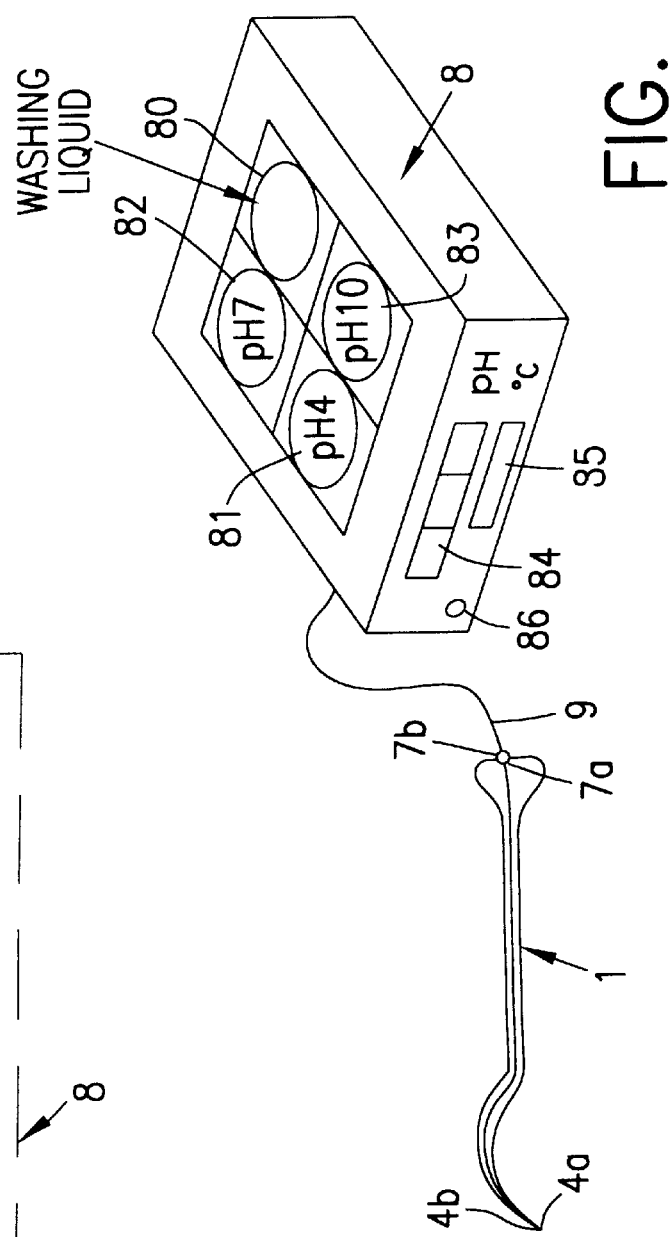
FIG. 5 is an electric circuit of an embodiment of the dental probe.

FIG. 5 shows an electric circuit of the dental diagnosis device used with the dental probe 1. The pH sensor (4a) and the temperature sensor (4b) of the dental probe (1) are connected to A/D transducer via an amplifier. In this example, the Gate G-Source S voltage (Vgs) works as an electric output signal of the pH sensor (4a), while the Drain D-Source S current (Ids) is maintained constant, connected to the constant current generator (means to provide current to the sensor). Output from the A/D transducer are then converted to pH and temperature value at the CPU (where signals from the sensor will be recorded in numbers) and shown on such a display device as liquid crystal display. The amplifier, A/D transducer, constant current generator, CPU, and display are contained in the box 8.

Figure 6:
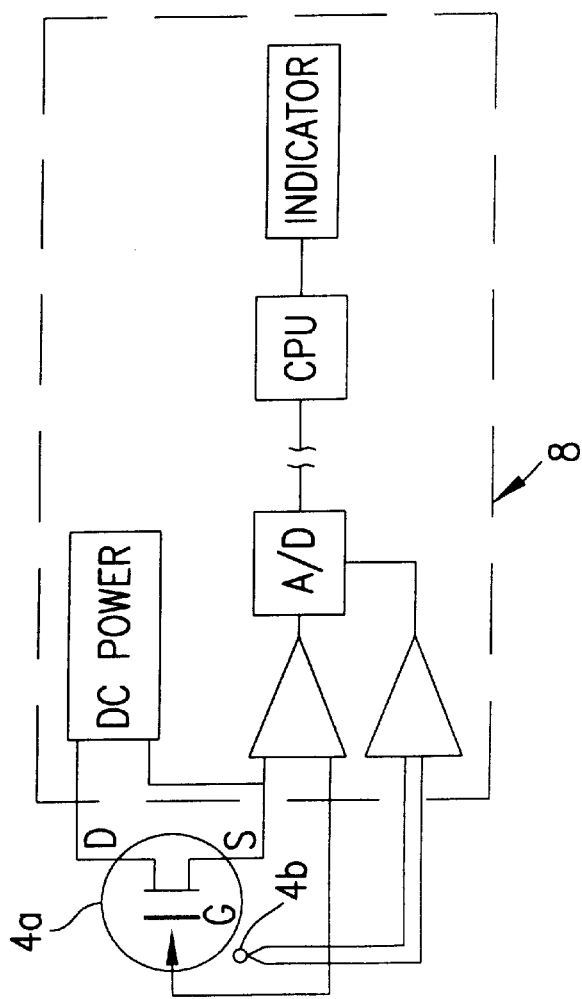
FIG. 6 is a diagonal view an embodiment of the dental probe.

FIG. 6 shows the dental probe 1 attached to the dental diagnosis device 8. The connector 7b at the end of the lead line 9 is coupled to the output terminal 7a of the dental probe 1. The connection is easily released, enabling the user to replace dental probes. The box 8 contains washing pool 80, buffer solutions 81–83 to store pH 4, 7, and 10 solution, respectively. It also contains a pH monitor 84, a temperature monitor 85, and a switch 86. Prior to the pH test with the dental probe 1, a test adjustment is made by soaking the pH sensor 4a into three buffer solutions. The CPU automatically processes the data, and draws a calibration curve onto the CPU memory. When the needle tip of the dental probe is inserted into the oral cavity, the user can determine he pH level of the diseased part, using the calibration curve.

We claim:

1. A dental probe for diagnostic use, said dental probe comprising:
   a) a handle having a distal end and a proximal end;
   b) a needle at said distal end of said handle for probing a desired part of the mouth;
   c) a pH sensor at the tip of said needle; and
   d) a wire having a first end and a second end, said first end attached to said pH sensor at said tip of said needle, said second end coupled to a dental diagnosis device, said dental diagnosis device for receiving output signals from said pH sensor.

2. The dental probe described in claim 1, wherein said pH sensor is an N-channel ISFET pH sensor.

3. The dental probe described in claim 1, wherein said wire is transparent, and wherein said transparent wire is embedded along the length of said dental probe between said distal end and said proximal end.

4. The dental probe described in claim 1, wherein said dental probe further includes a temperature sensor at said tip of said needle.

5. The dental probe described in claim 4, further including a second wire having a first end and a second end, said first end of said second wire attached to said temperature sensor at said tip of said needle, said second end of said second wire coupled to said dental diagnosis device, said dental diagnosis device for receiving signals from said temperature sensor.

6. The dental probe described in claim 5, wherein said dental probe is covered with a dielectric coating on all parts except near said pH sensor and said temperature sensor at said tip of said needle, and except on the wiring emanating from said pH sensor and said temperature sensor.

7. The dental probe described in claim 6, wherein said dental diagnosis device reads and displays data from said pH sensor and from said temperature sensor.

8. The dental diagnosis device described in claim 7, wherein said dental probe attached to said dental diagnosis device is replaceable.

9. The dental diagnosis device described in claim 7, wherein said dental diagnosis device draws pH calibration curves using buffer solutions.

10. The dental probe described in claim 1, wherein gradations are etched into said needle for recording the depth of gum pockets and other desired areas in the mouth, and wherein said needle has a hemispherical tip.

* * * * *